United States Patent [19]

Quincey

[11] 4,111,655

[45] Sep. 5, 1978

[54] ELECTRICALLY OPERATED AIR FRESHENERS

[75] Inventor: Edwin Albert Quincey, Seaford, England

[73] Assignee: Plessey Handel und Investments AG., Zug, Switzerland

[21] Appl. No.: 772,133

[22] Filed: Feb. 25, 1977

[30] Foreign Application Priority Data

Feb. 28, 1976 [GB] United Kingdom ............... 7973/76

[51] Int. Cl.² ........................... A61L 9/01; A61L 9/04
[52] U.S. Cl. .................................................. 422/124
[58] Field of Search .............. 21/74 R, 108, 121–127, 21/53, 55

[56] References Cited

U.S. PATENT DOCUMENTS

| 2,058,723 | 10/1936 | Rosenfeld | 21/74 R |
|---|---|---|---|
| 2,629,149 | 2/1953 | Yaffe | 21/108 |
| 2,747,101 | 5/1956 | Hammond | 21/74 R |
| 3,290,112 | 12/1966 | Gillenwater et al. | 21/108 |
| 3,661,323 | 5/1972 | Farris | 21/74 R |
| 3,990,848 | 11/1976 | Corris | 21/126 |
| 3,993,444 | 11/1976 | Brown | 21/108 |
| 4,035,451 | 7/1977 | Tringali | 21/126 |

Primary Examiner—Morris O. Wolk
Assistant Examiner—Bradley Garris
Attorney, Agent, or Firm—Fleit & Jacobson

[57] ABSTRACT

An air freshener device comprises a housing which accommodates a motor-driven fan, associated timing control means for providing cyclic operation of the fan in response to the actuation of switching means and a receptacle for deodorant material, the housing being formed in two cooperating parts which when moved relatively to one another from a normal position produce actuation of the switching means for the cyclic operation of the fan as well as providing through the housing one or more flow paths for air which is displaced by the fan over the deodorant material before being discharged to ambient atmosphere.

6 Claims, 8 Drawing Figures

ELECTRICALLY OPERATED AIR FRESHENERS

This invention relates to electrically-operated air fresheners and is directed to a small portable air freshner device of simple and relatively inexpensive construction.

According to the present invention there is provided an air freshener device comprising a housing which accommodates a motor-driven fan, associated timing control means for providing cyclic operation of said fan in response to the actuation of switching means, and a receptacle for deodorant material, said housing being formed in a plurality of co-operating parts which when moved relatively to one another from a normal position produce actuation of said switching means for the cyclic operation of the motor-driven fan as well as providing through said housing one or more flow paths for air which is displaced by the motor-driven fan over the deodorant material before being discharged to ambient atmosphere.

The air freshener device according to the invention is preferably operated from one or more batteries contained within the housing.

By way of example the present invention will now be described with reference to the accompanying drawings in which.

Figure 1:
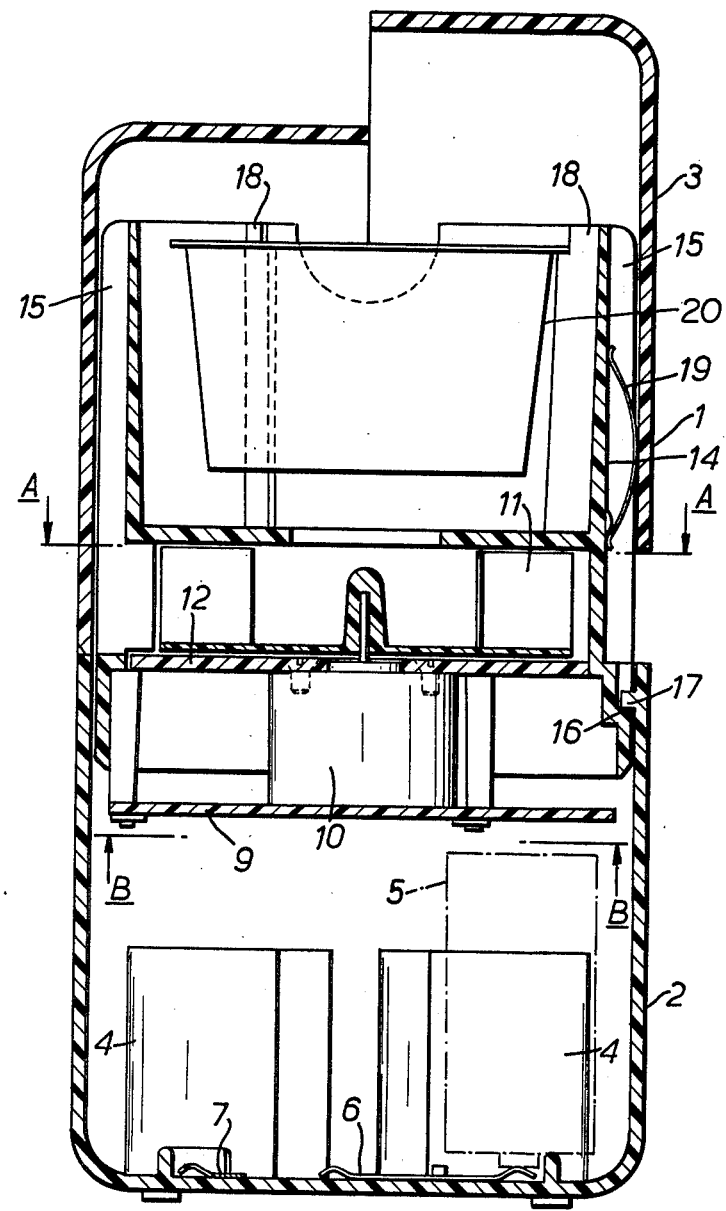
FIG. 1 is a diagrammatic sectional view of an air freshener device.
Figure 2:
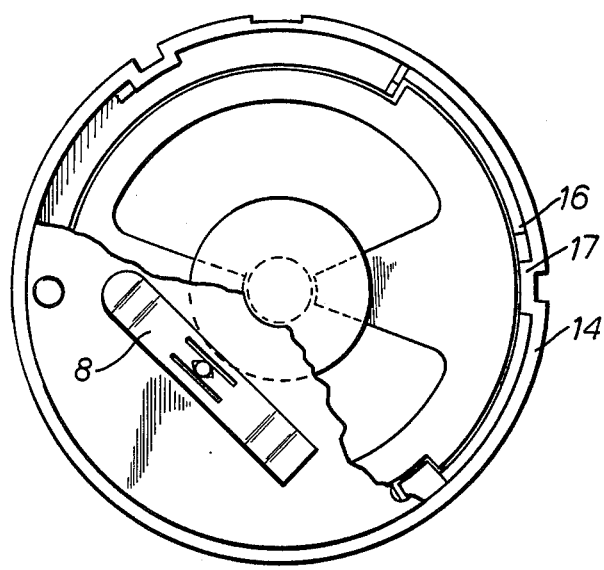
FIG. 2 is a sectional view taken along the line B—B in FIG. 1.
Figure 3:
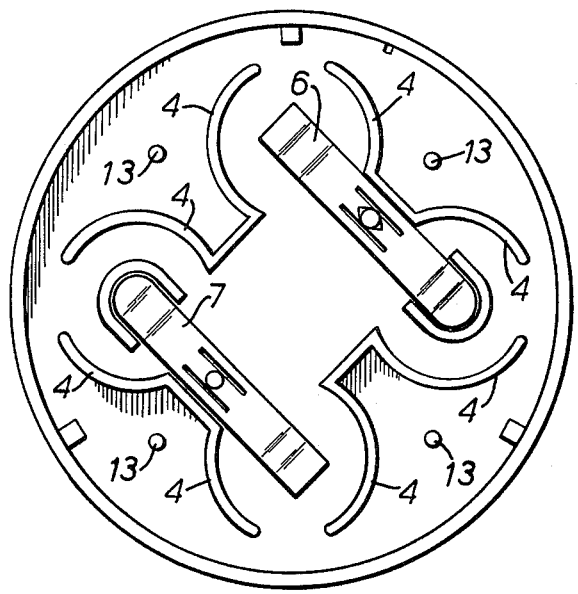
FIG. 3 is an inside view of the base of the air freshener device.
Figure 4:
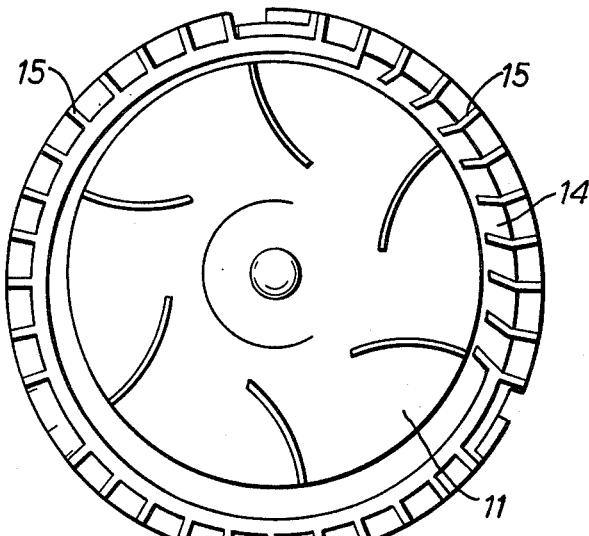
FIG. 4 is a sectional view taken along the line A—A of FIG. 1.
Figure 5:
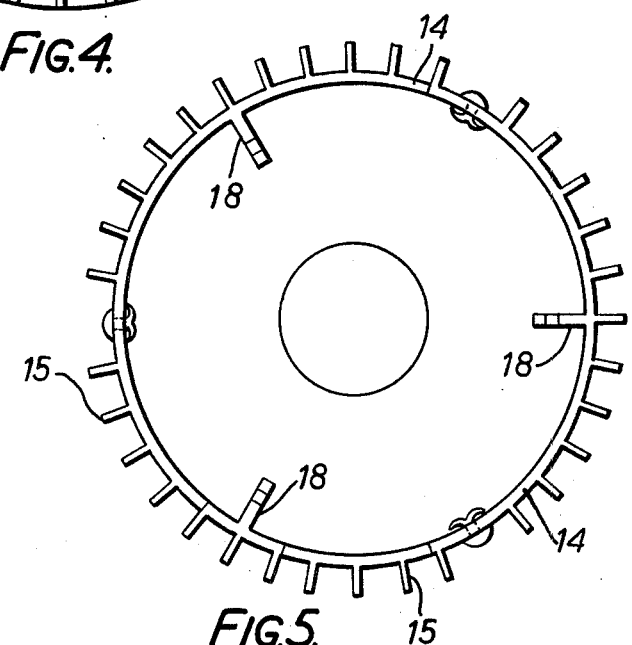
FIGS. 5 and 6 are plan and fragmentary side views, respectively, of an inner supporting structure of the device.
Figure 6:
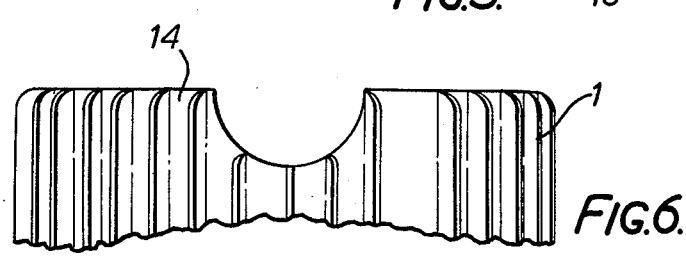

Referring to the drawings, the air freshener device illustrated comprises a two-part housing 1 of cylindrical shape. The housing parts 2 and 3 may be of moulded plastics construction. The lower housing part 2, the inside bottom view of which is shown in FIG. 2, provides cylindrical upstanding walls 4 for receiving batteries one of which is shown in dotted outline at 5 in FIG. 1, which will be electrically interconnected by means of metallic strip terminals 6 and 7 rivetted or otherwise secured to the base of the housing part 2. The upper terminals of the batteries will be interconnected by further strip terminals one of which is shown at 8 in FIG. 2 conveniently secured to the underside of a circular insulating board 9 which carries timing circuit control components which are shown as part of the timing control circuit in FIG. 7. This insulating board 9 is attached to the base of a small motor 10 for driving fan 11 which in turn is secured, as by screws, to the underside of an apertured motor support plate 12. The motor 10 and its support plate 12 and board 9 may be supported on pillars 13 (FIG. 3) upstanding from the base of the housing part 2. A moulded plastics structure 14 of hollow cylindrical form which is provided around its periphery with vertically extending vanes 15 to provide channels for the passage of air sits on top of the apertured motor plate 1 and is locked to the housing base part 2 by means of shouldered parts such as the part 16 which fits underneath projections such as the projections 17 on the part 2. The vaned structure 14 supports a cup-shaped receptacle 20 which receives a block of deodorant material (not shown) and which rests on shouldered support vanes or ribs 18 (FIGS. 1 and 5) projecting radially inwards from the structure 13. The housing is arranged to be closed by the cover part 3 which is slidably mounted for vertical movement with respect to the support structure 14 by means of bowed springs one of which is shown at 19 which are located between the structure 14 and the cover part 3. The friction between the ends of these springs and the structure 14 and the engagement of indentations in a central support enables the cover 3 to be raised and left in the raised position as shown in the right-hand section of FIG. 1. The cover 3 as it is raised so as to open a number of paths for air-flow through the device actuates the arm of an electric switch shown at SW1 in FIG. 7 so that the batteries are connected through the timing circuit on the board 9 to the motor-driven fan. The fan will be driven by the motor 10 cyclically under the control of timing circuit so that the fan draws air over the deodorant material before being discharged to ambient atmosphere between the separated cover 3 and base part 2 of the housing.

It may be arranged that whilst the cover part 3 is open the motor 10 will be operated for 30 seconds to 1 minute say, and will then be rendered inoperative by the timing circuit for 15 to 20 minutes before being re-operated again.

Figure 7:
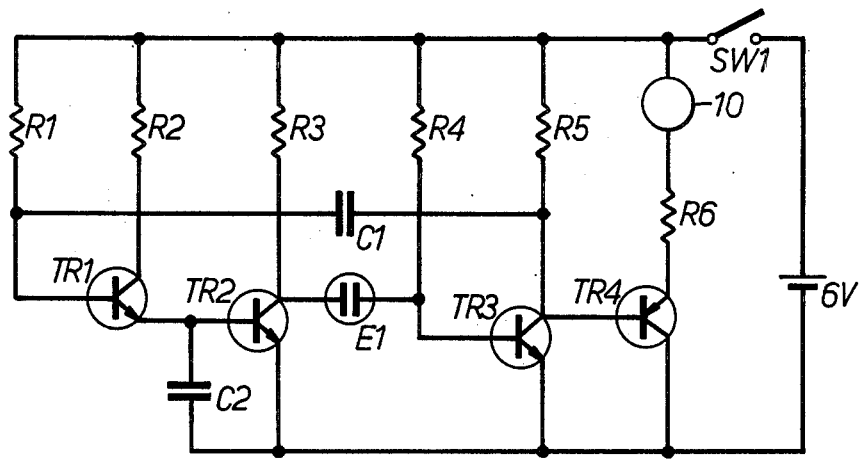
FIG. 7 is a circuit diagram of a timing control circuit forming part of the air freshener device; and, FIG. 8 is a perspective view of the device of FIG. 1.
Figure 8:
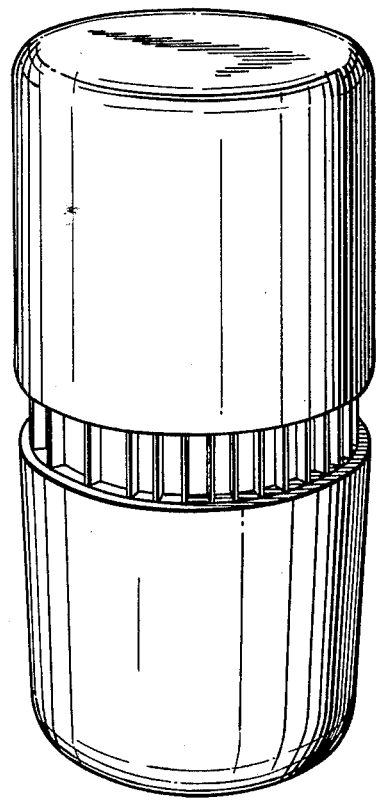

Referring now to FIG. 7 of the drawings, this shows the timing control circuit for the fan motor 10. The cyclic operation of the fan is produced by the oscillatory action of transistors TR1, TR2, TR3 and TR4 having associated resistors R1 to R6 and which are set in oscillation in response to the application of battery voltage (6V) to them when the switch SW1 is actuated when the housing cover 3 is drawn away from the base 2. Time delay capacitors C1 and C2 and "E" cell E1 are also included in the timing circuit.

Access to the deodorising cup-shaped receptacle 20 may be had by removal of the cover part 3 from the device whilst the batteries may be reached by the removal of the structure 14 and the motor-driven fan from the housing.

What we claim is:

1. An air freshener device comprising a housing having first and second cooperating housing portions movable relative to each other between a first position, wherein said housing portons define a closed chamber, and a second position, wherein at least one flow path is defined from the interior of said housing to the exterior of said housing, an electric motor mounted within said housing, a fan mouned within said housing and connected to said electric motor and operated thereby, an open container for volatile deodorant material mounted within said housing, said container adapted to remain open independent of the relative position of said first and second cooperating housing portions, timing means mounted within said housing for cyclic operation of said electric motor, and switch means mounted within said housing and interconnected with said timing means for providing cyclic operation of said fan when said first and second housing portions are in said second position, and for preventing cyclic operation of said fan when said first and second housing portions are in said first position.

2. An air freshener device as claimed in claim 1 in which the housing provides means for accommodating one or more batteries for operating the fan.

3. An air freshener device as claimed in claim 1, in which the timing means comprises a transistor oscillator circuit.

4. An air freshener device as claimed in claim 1, wherein said open container of deodorant material is interconnected with said first portion of said housing, and wherein said fan is mounted within said housing at a position whereby said open container of deodorant material is in the air flow path of said fan.

5. An air freshener device as claimed in claim 4, wherein said first and second cooperating housing portions define a gap therebetween when in said second position, said gap defining said flow path, whereby when said first and second housing portions are in said second position, the fan is cyclically operated to cause air flow around said open container and through said gap.

6. An air freshener device as claimed in claim 5 further comprising a supporting structure for supporting said open container at a position within said housing in the air flow path, said supporting structure comprising air directing vane means for guiding the air flow to said gap.

* * * * *